(12) United States Patent
Taniguchi et al.

(10) Patent No.: US 7,951,553 B2
(45) Date of Patent: May 31, 2011

(54) METHOD OF ASSAYING GLYCATED PROTEIN

(75) Inventors: Yuriko Taniguchi, Ryugasaki (JP); Hiroyuki Ebinuma, Ryugasaki (JP); Kazunori Saito, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 1039 days.

(21) Appl. No.: 10/580,000

(22) PCT Filed: Nov. 18, 2004

(86) PCT No.: PCT/JP2004/017195
§ 371 (c)(1),
(2), (4) Date: Feb. 21, 2007

(87) PCT Pub. No.: WO2005/049857
PCT Pub. Date: Jun. 2, 2005

(65) Prior Publication Data
US 2008/0233605 A1    Sep. 25, 2008

(30) Foreign Application Priority Data

Nov. 19, 2003    (JP) ................................ 2003-389891

(51) Int. Cl.
*C12Q 1/37*    (2006.01)
(52) U.S. Cl. .................... 435/23; 435/4; 435/6; 435/7.1
(58) Field of Classification Search .................... None
See application file for complete search history.

(56) References Cited

U.S. PATENT DOCUMENTS

2003/0162242 A1    8/2003    Yonehara

FOREIGN PATENT DOCUMENTS

| EP | 0 526150 | 7/1992 |
|---|---|---|
| EP | 1 223 224 | 7/2002 |
| EP | 1 291 416 | 3/2003 |
| JP | 03-155780 | 7/1991 |
| JP | 5-33997 | 5/1993 |
| JP | 11-127895 | 5/1999 |
| JP | 2000-333696 | 12/2000 |
| JP | 2001-057897 | 3/2001 |
| JP | 2001-95598 | 4/2001 |
| JP | 2001-204494 | 7/2001 |
| JP | 2001-204495 | 7/2001 |
| JP | 2003-235585 | 8/2003 |
| JP | 2003-274976 | 9/2003 |
| WO | 02/06519 | 1/2002 |
| WO | 02/061119 | 8/2002 |
| WO | WO 2005/017136 A1 | 2/2005 |
| WO | WO 2005/049858 A1 | 6/2005 |

OTHER PUBLICATIONS

Watanabe et al. (Agri. Biol. Chem. vol. 54, No. 4, pp. 1063-1064, 1990).*
Sakurabayashi, Ikunosuke, et al. "New Enzymatic Assay for Glycohemoglobin", Clinical Chemistry, American Association for Clinical Chemistry, XP009008806, vol. 49, No. 2, Jan. 1, 2003, pp. 269-274.
Hirokawa, Kozo, et al. "Molecular cloning and expression of novel fructosyl peptide oxidases and their application for the measurement of glycated protein", Biochemical and Biophysical Research Communications, Academic Press Inc., XP004465110, vol. 311, No. 1, Nov. 7, 2003, pp. 104-111.
U.S. Appl. No. 10/592,800, filed Sep. 14, 2006, Taniguchi, et al.
U.S. Appl. No. 10/592,700, filed Sep. 13, 2006, Taniguchi, et al.
U.S. Appl. No. 10/579,765, filed May 18, 2006, Taniguchi, et al.
Japanese Official Communication dated Nov. 16, 2010 w/English Translation.
List of Enzyme—Formaldehyde dehydrogenase (Toyobo Enzyme) Jul. 1, 1996, pp. 1-4.
List of Enzyme-Glutamate dehydrogenase dehydrogenase (Toyobo Enzyme), Jul. 1, 1996, pp. 1-4.
Toyobo Enzymes—Reference which are dated in the contents of References 4-5, Jul. 1, 1996 and its English translation of relevant portions as pointed out in the Official Communication.
Taiwanese Office Action dated Nov. 30, 2010 as received in the corresponding Taiwanese Patent Application No. 093135701.

* cited by examiner

*Primary Examiner* — Hope A Robinson
(74) *Attorney, Agent, or Firm* — Oblon, Spivak, McClelland, Maier & Neustadt, L.L.P.

(57) ABSTRACT

The present invention provides a convenient, efficient method for assaying glycated protein, fructosyl peptide, or fructosyl amino acid which can be performed with reduced effect of fructosyl lysine compounds. The invention also provides a reagent for the assay.
The invention is directed to a method for reducing the effect of a fructosyl lysine compound in an assay of fructosyl peptide or fructosyl amino acid contained in a sample, characterized by including causing an enzyme for assaying fructosyl peptide or fructosyl amino acid to act specifically on fructosyl peptide or fructosyl amino acid at a pH of 4.0 to 7.0 and measuring the product at a pH of 4.0 to 7.0; and a method for assaying glycated protein through the above method.

10 Claims, 1 Drawing Sheet

METHOD OF ASSAYING GLYCATED PROTEIN

CROSS-REFERENCE TO RELATED APPLICATIONS

The present application is a 371 application of PCT/JP04/17195 filed Nov. 18, 2004 and claims the benefit of JP 2003-389891 filed Nov. 19, 2003.

TECHNICAL FIELD

The present invention relates to a method for assaying glycated protein, glycated peptide, or glycated amino acid contained in a sample. This invention also relates to a reagent to be used for the method.

BACKGROUND ART

Glycated protein is a non-enzymatically glycated protein, which is an Amadori compound forming from the Amadori rearrangement following the formation of a Schiff base between the aldehyde group of a sugar and the amino group of a protein. Glycated proteins are ubiquitously present in the living body. The concentration level of glycated protein in blood is influenced largely by the concentration of monosaccharide (e.g., glucose) dissolved in serum. Exemplary glycated proteins include proteins whose α-amino group at the amino terminus is glycated (e.g., glycated hemoglobin), and proteins whose ε-amino groups contained in internal lysine residues are glycated (e.g., glycated albumin). The concentration of glycated albumin in serum or the ratio of glycated hemoglobin to non-glycated hemoglobin present in erythrocytes reflects the average sugar level in a certain period and therefore is used as an index for clinical diagnosis, such as diagnosis of diabetes, control of pathological condition, or judgment of therapeutic effect.

Among the assays of glycated protein, there is a method called "enzyme method" that can be performed with ease and is adaptable to an automatic analyzer commonly used in clinical laboratories (e.g., Patent Document 1). The enzyme method consists of a pretreatment step needed for reaction of a protease with glycated protein contained in a sample to thereby release glycated peptide or glycated amino acid, which serves as a substrate in the next step, and an assay step needed for reaction of the free substrate with a glycated peptide-specific enzyme or a glycated amino acid-specific enzyme (e.g., oxidase) to thereby produce a detectable substance (e.g., hydrogen peroxide) and measuring the substance.

However, there has been a problem with the enzyme methods reported so far, in that a protease employed in the pretreatment step and a specific enzyme employed in the assay step have no sufficient ability to recognize differences between glycated protein, glycated peptide, and glycated amino acid (hereinafter may be collectively referred to as "glycated protein or the like"), and therefore, if the target glycated protein coexists with another glycated protein not being targeted for assay, both proteins react with the specific enzyme and thereby undermines the specificity of said method.

Examples of glycated peptide-specific enzyme or glycated amino acid-specific enzyme which is used in the pretreatment step include an oxidase which is produced from a bacterium belonging to the genus *Corynebacterium* (see, for example, Patent Document 2), and an oxidase which is produced from a bacterium belonging to the genus *Aspergillus* (see, for example, Patent Document 3). These enzymes effectively react with glycated amino acid, but tend to remain unreactive against glycated peptide. Recently, an enzyme which is obtained through modification of a fructosyl amino acid oxidase (Patent Document 4) and a fructosyl peptide oxidase derived from a filamentous fungus (Patent Document 5) have been reported. These oxidases are reported to react specifically with a glycated peptide, especially fructosyl valylhistidine, at pH 8.0.

In the measurement of glycated hemoglobin through use of such a fructosyl amino acid oxidase, specificity of the oxidase is derived from the difference in reactivity of the oxidase with fructosyl valine (valine at the amino terminal of hemoglobin β-subunit is glycated) or fructosyl valylhistidine (one amino acid residue is further added to fructosyl valine) and with ε-fructosyl lysine (lysine residue(s) in a protein is glycated). A hemoglobin molecule has 44 lysine residues. Therefore, even when the reactivity of an oxidase with ε-fructosyl lysine is low, the total effect of the ε-fructosyl lysine residues should not be ignored. Furthermore, a compound which contains fructosyl lysine and is derived from hemoglobin or other plasma proteins (e.g., glycated albumin) or derived from food or drug (hereinafter may be referred to as "fructosyl lysine compound") has to carry a risk that could lead to positive error. Such a risk is hard to prevent, as long as any conventional assay method is used.

[Patent Document 1] JP-A-1999-127895
[Patent Document 2] Japanese Patent Publication (kokoku) No. H5-33997 (1993)
[Patent Document 3] JP-A-1991-155780
[Patent Document 4] JP-A-2001-95598
[Patent Document 5] JP-A-2003-235585

DISCLOSURE OF THE INVENTION

Problem(s) to be Solved by the Invention

Accordingly, the present invention provides a convenient, efficient method for assaying glycated protein, fructosyl peptide, or fructosyl amino acid, which can be applied to a variety of automatic analyzers while reducing effect of fructosyl lysine compounds, and a reagent employed in the method.

Means for Solving the Problem

In view of the foregoing, the present inventors have performed extensive studies and have found that, in the assay of glycated protein, fructosyl peptide, or fructosyl amino acid, effect of fructosyl lysine compounds present in the reaction system can be reduced by causing an enzyme for assaying fructosyl peptide or fructosyl amino acid (hereinafter may be referred to as "assay enzyme") to act specifically on fructosyl peptide or fructosyl amino acid at a pH of 4.0 to 7.0. The present invention has been accomplished based on this finding.

The present invention provides a method for reducing effect of a fructosyl lysine compound in assay of fructosyl peptide or fructosyl amino acid, characterized by comprising causing an enzyme for assaying fructosyl peptide or fructosyl amino acid to act specifically on fructosyl peptide or fructosyl amino acid at a pH of 4.0 to 7.0 and measuring the resultant product at a pH of 4.0 to 7.0.

The present invention also provides a method for reducing effect of a fructosyl lysine compound in glycated protein assay of a sample, characterized by comprising treating the glycated protein-containing sample with a protease to thereby release free fructosyl peptide or fructosyl amino acid, causing an enzyme for assaying fructosyl peptide or fructosyl amino acid to act specifically on the released fructosyl peptide or fructosyl amino acid at a pH of 4.0 to 7.0, and measuring the resultant product at a pH of 4.0 to 7.0.

The present invention also provides a reagent for assaying glycated protein with reduced effect of a fructosyl lysine compound, containing at least (A) a protease, (B) an oxidase which specifically acts on fructosyl peptide or fructosyl amino acid at a pH of 4.0 to 7.0 to thereby produce hydrogen peroxide, and (C) a reagent for measuring hydrogen peroxide.

The present invention also provides a method for reducing effect of a fructosyl lysine compound in assay of fructosyl peptide or fructosyl amino acid, characterized by comprising causing at least the following (A) to (C) to act on fructosyl peptide or fructosyl amino acid at a pH of 4.0 to 7.0: (A) an enzyme for assaying fructosyl peptide or fructosyl amino acid, (B) a reagent for measuring hydrogen peroxide, and (C) a glucosone-oxidizing and decomposing enzyme.

The present invention also provides a method for reducing effect of a fructosyl lysine compound in an assay of glycated protein contained in a sample, characterized by comprising treating a glycated protein-containing sample with a protease to thereby release fructosyl peptide or fructosyl amino acid, and causing at least the following (A) to (C) to act on the released fructosyl peptide or fructosyl amino acid at a pH of 4.0 to 7.0:(A) an enzyme for assaying fructosyl peptide or fructosyl amino acid, (B) a reagent for measuring hydrogen peroxide, and (C) a glucosone-oxidizing and decomposing enzyme.

EFFECTS OF THE INVENTION

The present invention provides an accurate assay of glycated protein, fructosyl peptide, or fructosyl amino acid while reducing effect of fructosyl lysine compounds. The method according to the present invention can be performed through a simple operation and thus can be applied to various analysis methods. Therefore, the method of the present invention is very useful in clinical tests.

BEST MODE FOR CARRYING OUT THE INVENTION

Figure 1:
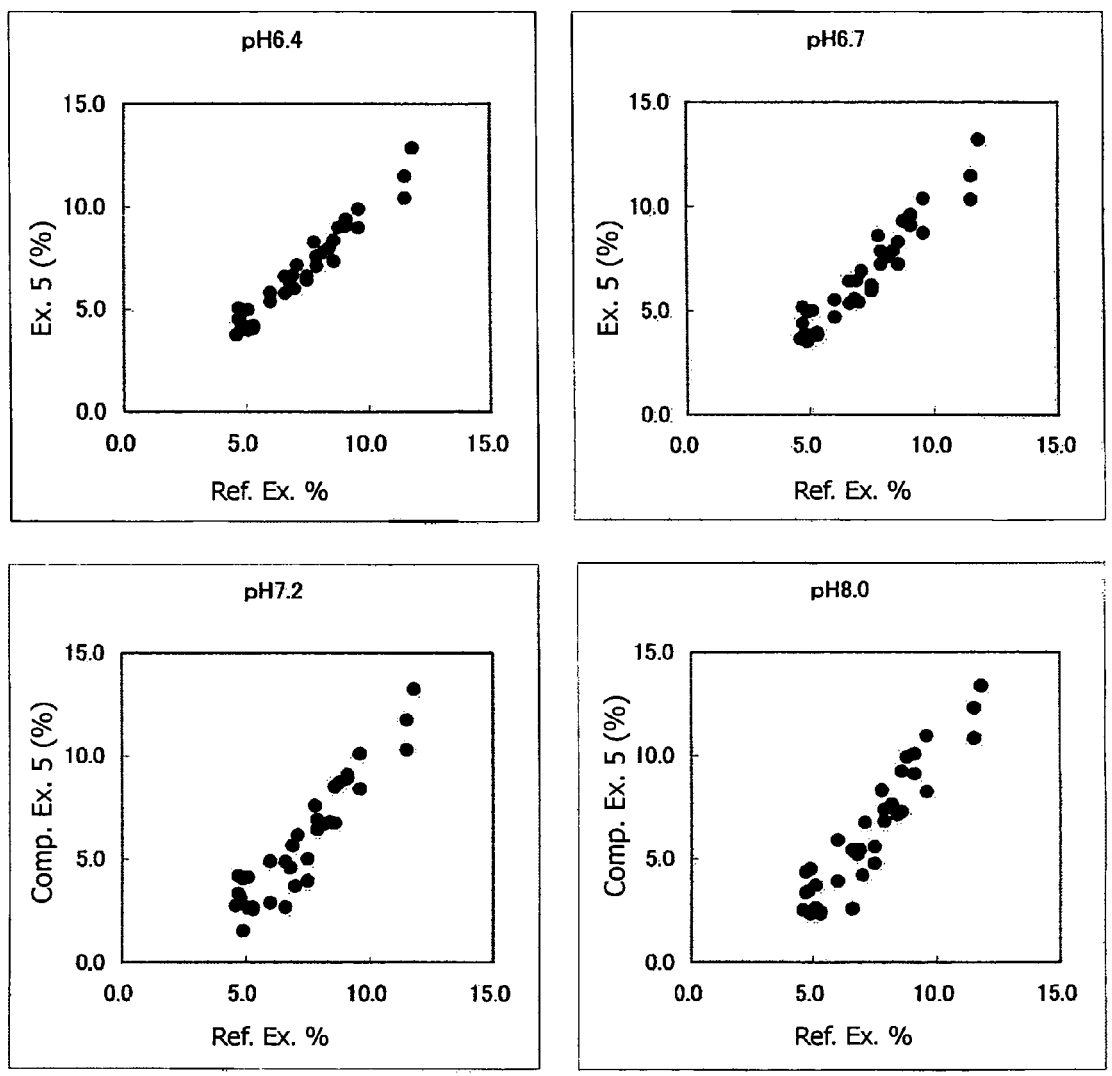
FIG. 1 shows correlation between the hemoglobin A1c values (%) obtained from the method of the present invention (Example 5) and the hemoglobin A1c values (%) obtained from a referential method, as well as correlation between the hemoglobin A1c values (%) obtained from the method of Comparative Example 5 and the hemoglobin A1c values (%) obtained from the referential method.

No particular limitation is imposed on the glycated protein to be assayed, so long as the glycated protein is formed through non-enzymatic binding of a protein with an aldose such as glucose. Examples of the glycated protein include glycated hemoglobin and glycated albumin. Of these, glycated hemoglobin, especially hemoglobin A1c (HbA1c) is preferred.

Examples of a biological sample containing glycated protein include whole blood, hemocytes, serum, plasma, cerebrospinal fluid, sweat, urine, lachrymal fluid, saliva, skin, mucosa, and hair. Glycated protein is also contained in a wide range of foods such as juice and seasonings. Of these, whole blood, hemocytes, serum, and plasma are preferred. The sample may be measured as is; i.e., without undergoing any treatment. Alternatively, prior to the measurement, the sample may be filtered or dialyzed. In addition, glycated protein to be measured may be appropriately subjected to concentration, extraction, or dilution with water or a buffer, which is described hereinbelow.

In the method of the present invention, firstly, glycated protein is treated with a peptidase to release fructosyl peptide or fructosyl amino acid. No particular limitation is imposed on the protease, so long as the protease has proteolysis or peptidolysis activity. Preferably, there is employed a protease which can efficiently release fructosyl peptide or fructosyl amino acid (preferably fructosyl valylpeptide or fructosyl valine) in a short period of time. No particular limitation is imposed on the origin of protease, and protease may be derived from a microorganism, an animal, a plant, or the like. Specific examples of the protease include commercially available reagents for study purposes, such as proteinase K, trypsin, bromelain, carboxypeptidase, papain, pepsin, and aminopeptidase; and commercially available reagents for industrial use such as Neutral proteinase, Toyozyme NEP (these two are products of Toyobo, Ltd.), acid protease, alkaline protease, Molsin, AO protease, peptidase (these five are products of Kikkoman Corporation), Sumizyme CP, Sumizyme TP, Sumizyme LP50D (these three are products of Shin Nihon Chemical Co., Ltd.), Thermoase PC10F, Protin PC, Protin PC10F, Protin PS10, Protin NY10, Protin NL10, Protin NC25 (these seven are products of Daiwa Kasei K.K.), Actinase AS (product of Kaken Pharmaceutical Co., Ltd.), Pronase E (product of Roche), Umamizyme, Protease S "Amano" G, Protease A "Amano" G, and Protease P "Amano" 3G (these four are products of Amano Enzyme Inc.). Effect of the protease may be determined in the following manner: the protease is reacted with fructosyl peptide or the like, the glycated protein or fructosyl peptide before reaction and resultant product after reaction are subjected to capillary electrophoresis, and the results are analyzed and compared between before and after the reaction with the protease. The protease may be employed singly or in combination of two or more species. The protease is preferably derived from a microorganism belonging to the genus *Bacillus*, *Aspergillus*, or *Streptomyces*; or produced from a gene of such a microorganism; or belongs to metalloproteinase, neutral protease, acid protease or basic protease. Examples of enzymes derived from the genus *Bacillus* include Protin PC10F, Protin NC25 (these two are products of Daiwa Kasei K.K.), and Toyozyme NEP (product of Toyobo, Ltd.). Examples of the enzymes derived from the genus *Aspergillus* include Molsin (product of Kikkoman Corporation). Examples of enzymes derived from the genus *Streptomyces* include Actinase AS, Actinase AF, Actinase E (these three are products of Kaken Pharmaceutical Co., Ltd.), and protease Type-XIV (product of Sigma). These enzymes may be employed singly or in combination (e.g., combination of proteinase K and Toyozyme NEP etc.).

No particular limitation is imposed on the concentration of the enzyme during actual use, so long as the protease can efficiently release a free fructosyl peptide of interest or a free fructosyl amino acid of interest. An appropriate concentration of the protease may be experimentally determined in consideration of the specific activity or a similar factor of the protease. For example, the protease derived from the genus *Aspergillus* (e.g., Molsin, product of Kikkoman Corporation) is added in a concentration of 0.0001 to 50 mg/mL, preferably 0.001 to 20 mg/mL. Adjustment of pH for the protease treatment is not necessarily performed, but the pH may be adjusted to a value which is optimal for reaction of the enzyme, within a range of 3.0 to 11.0. Adjustment of pH is carried out through use of an appropriate pH regulating agent such as a buffer, which is described hereinbelow. The treatment temperature is preferably 10 to 40° C.

No particular limitation is imposed on the buffer. Examples of the buffer include phosphate, phthalate, citrate, Tris, maleate, succinate, oxalate, tartrate, acetate, and Good's (MES, PIPES, ADA, etc.) buffers. No particular limitation is imposed on the concentration of the buffer. The concentration of the buffer may be 0.00001 to 2 mol/L, preferably 0.001 to 1 mol/L.

Examples of a free fructosyl peptide or a free fructosyl amino acid which is obtained through treatment of a sample with a protease include fructosyl valylhistidine and fructosyl valine. A biological sample or a food product before undergoing treatment with a protease already contains fructosyl peptide or fructosyl amino acid, which is formed through binding of glucose to free peptide or amino acid released through digestion of glycated protein and through Amadori rearrangement of the product. These fructosyl peptide and fructosyl amino acid are also included in the free fructosyl peptide or fructosyl amino acid with which an assay enzyme is reacted.

The free fructosyl peptide or free fructosyl amino acid can be assayed by reacting an assay enzyme with fructosyl peptide or fructosyl amino acid and then measuring the substance obtained from the reaction.

No particular limitation is imposed on the assay enzyme which is reacted with fructosyl peptide or fructosyl amino acid, so long as the assay enzyme can metabolize free fructosyl peptide or free fructosyl amino acid. Examples include fructosyl amino acid oxidase (JP-A-2003-79386 and WO97/20039 pamphlet), ketoamine oxidase (JP-A-1993-19219), and fructosyl peptide oxidase (JP-A-2001-95598 and JP-A-2003-235585). Of these, fructosyl peptide oxidase is preferred. The enzyme may be derived from a microorganism, an animal, a plant, etc., or may be genetically engineered. In addition, the enzyme may or may not be chemically modified. The enzyme may be in solution form or dry form, and may be carried on or bound to an insoluble carrier. The enzyme may be used singly or in combination of two or more species.

The amount of the enzyme employed varies depending on the type of the enzyme. The enzyme is employed preferably in an amount of 0.001 to 1,000 U/mL, particularly preferably 0.1 to 500 U/mL. The enzyme concentration may be experimentally determined appropriately in consideration of the specific activity of the enzyme. The pH conditions under which the enzyme is reacted are determined by use of a buffer in consideration of the optimal pH of the enzyme, and adjusted to pH 4.0 to 7.0, preferably pH 4.0 to 6.7, where the effect of the present invention can be ensured. The reaction temperature may be appropriately selected from a temperature range which is ordinarily employed in enzyme reactions; e.g., 10 to 40° C. Like the above, no particular limitation is imposed on the buffer. Examples of the buffer include phosphate, phthalate, citrate, Tris, maleate, succinate, oxalate, tartrate, acetate, and Good's buffers. Of these, phosphate, citrate, and ADA (N-(2-acetamide)iminodiacetic acid) buffers are preferred because they ensure excellent storage stability of enzymes for measurement of fructosyl peptide or fructosyl amino acid. No particular limitation is imposed on the concentration of the buffer, and the concentration is preferably 0.00001 to 2 mol/L, more preferably 0.001 to 1 mol/L.

In accordance with needs, the above enzyme for measurement may be used in combination with another enzyme, a coenzyme, an oxidizable color producing reagent, etc. Examples of the enzyme include peroxidase, diaphorase, and amino acid-metabolizing enzymes which do not react with a substrate, fructosyl valine. Alternatively, an enzyme such as ascorbic acid oxidase or bilirubin oxidase may be employed to treat other components present in blood. Examples of the coenzyme include nicotinamide adenine dinucleotide (NAD), reduced nicotinamide adenine dinucleotide (NADH), nicotinamide adenine dinucleotide phosphate (NADP), reduced nicotinamide adenine dinucleotide phosphate (NADPH), thio-NAD, and thio-NADP.

No particular limitation is imposed on the oxidizable color producing reagent, so long as the oxidizable color producing reagent is reacted with hydrogen peroxide to thereby develop color. Examples include a combination of 4-aminoantipyrine and a phenol compound, a naphthol compound, or an aniline compound, and a combination of 3-methyl-2-benzothiazolinonehydrazone and an aniline compound. Examples of the phenol compound which may be combined with 4-aminoantipyrine include phenol, p-chlorophenol, 2,4-dichlorophenol, 2,4-dibromophenol, and 2,4,6-trichlorophenol. Examples of the aniline compound which may be combined with 4-aminoantipyrine include N,N-dimethylaniline, N,N-diethylaniline, N,N-dimethyl-m-toluidine, N,N-diethyl-m-toluidine, N-ethyl-N-sulfopropyl-m-toluidine, N-ethyl-N-(2-hydroxy-3-sulfopropyl)-m-toluidine (TOOS), N-ethyl-N-(3-methylphenyl)-N'-acetylethylenediamine, 3-methyl-N-ethyl-N-(hydroxyethyl)aniline, N-ethyl-N-(2-hydroxy-3-sulfopropyl)aniline (ALOS), N-ethyl-N-(3-sulfopropyl) aniline (ALPS), N,N-dimethyl-m-anisidine, and N-ethyl-N-(2-hydroxy-3-sulfopropyl)-m-anisidine (ADOS) etc. Other examples include N-(carboxymethylaminocarbonyl)-4,4'-bis (dimethylamino)-diphenylamine-sodium salt (DA-64), 10-(carboxymethylaminocarbonyl)-3,7-bis(dimethylamino)-phenothiazine-sodium salt (DA-67), 10-N-methylcarbamoyl-3,7-dimethylamino-10H-phenothiazine (MCDP), N,N,N',N',N'',N''-hexa-3-sulfopropyl-4,4',4''-triaminotriphenylmethane (TPM-PS), diaminobenzidine, hydroxyphenylpropionic acid, tetramethylbenzidine, and orthophenylenediamine etc.

Examples of a substance produced through reaction of the assay enzyme with fructosyl peptide or fructosyl amino acid include peptide, hydrogen peroxide, and glucosone etc. The assay of the free fructosyl peptide or fructosyl amino acid can be performed through measurement of such a produced substance. Of the listed compounds, hydrogen peroxide is preferred, since the measurement can be performed in a simple manner in a short period of time. Hydrogen peroxide may be determined through, for example, a method employing an oxygen electrode, and an enzymatic method employing either a peroxidase or a diaphorase and the above coloring agent, with the latter being preferred.

Typically, the measurement of hydrogen peroxide is carried out directly after the step of reacting the assay enzyme with fructosyl peptide or fructosyl amino acid to produce hydrogen peroxide. The pH of the solution in which hydrogen peroxide is to be measured is adjusted with a buffer to a pH of 4.0 to 7.0, preferably 4.0 to 6.7. The degree of the color developed (change in absorbance) is measured by means of a spectrophotometer and is compared with one of a standard fructosyl peptide or fructosyl amino acid or the like having a known concentration. Thus, glycated protein, fructosyl peptide, or fructosyl amino acid contained in a sample can be determined.

The method for assaying glycated protein according to the present invention includes a step of releasing free fructosyl peptide or fructosyl amino acid and a step of measuring the released free fructosyl peptide or fructosyl amino acid. In the present invention, these steps may be performed separately, or may be performed in a single process; i.e., performed serially and directly one after another.

In the method for assaying glycated protein according to the present invention, the pH of the reaction mixture or the solution to be measured is adjusted to 4.0 to 7.0, preferably 4.0 to 6.7. This adjustment reduces effect of the assay enzyme of fructosyl peptide or fructosyl amino acid on fructosyl lysine compounds. Therefore, adjustment of pH to fall within the above range is essential in the step of measuring free fructosyl peptide or fructosyl amino acid.

The reagent for assaying glycated protein according to the present invention which provides reduced effect of fructosyl lysine compounds includes at least (A) a protease, (B) an oxidase which produces hydrogen peroxide by acting specifically on fructosyl peptide or fructosyl amino acid at a pH of 4.0 to 7.0, and (C) a reagent for determining hydrogen peroxide. In addition, sensitivity of the assay can be enhanced by reacting the oxidase described above in (B) with fructosyl peptide or fructosyl amino acid to produce glucosone, and reacting a glucosone-oxidizing and decomposing enzyme with the glucosone to thereby produce hydrogen peroxide (JP-A-2000-333696). The glucosone-oxidizing and decomposing enzyme is preferably at least one oxidase selected from the group consisting of glucose oxidase, β-galactosidase, and pyranose oxidase. The enzymes and the reagents are as described above. Besides, when glycated hemoglobin, especially hemoglobin A1c is assayed, a pretreatment agent which releases hemoglobin from erythrocytes to provide hemoglobin for the assay or a similar agent may be employed. Further, there may be incorporated into the reagent an enzyme for treating impurities contained in blood; a reaction-regulating agent; a stabilizer for the reagent; a salt such as sodium chloride, potassium chloride, or potassium ferrocyanide; a tetrazolium salt for removing effect of a reducing substance; an antibiotic serving as a preservative; sodium azide; etc.

Examples of the pretreatment agent include anionic surfactants and nonionic surfactants (e.g., TRITON® X-100, t-octylphenoxypolyethoxyethanol) selected from among polyoxyethylene derivatives. The amount of the surfactant employed is 0.0001 to 10%, preferably 0.001 to 1%, with respect to the sample, which has according to needs undergone filtration, dialysis, or a similar treatment.

The reagent for assaying glycated protein according to the present invention may be provided not only in solution form, but also in a dry form or in gel form. The reagent of the present invention may be packed in a glass vial, a plastic container, etc., or may be applied to or impregnated into an insoluble carrier. Examples of the insoluble carrier include particulate/spherical carriers made of, for example, latex, glass, and colloid; flat plate carriers made of, for example, semiconductor or glass; and film-like or filament-like carriers such as those made of paper or nitrocellulose.

EXAMPLES

The present invention will next be described in more detail by way of examples, which should not be construed as limiting the invention thereto.

Example 1

Measurement of Fructosyl Amino Acid (1) Preparation of Samples

Fructosyl valine (fV), fructosyl valylhistidine (fVH) (these two are products of BioQuest), and ε-fructosyl lysine (fK) (product of Kikkoman Corporation) were individually dissolved in 20 mmol/L phosphate buffer (pH 7.0) to prepare samples (0.3 mmol/L each).

(2) Measurement of Samples

The prepared samples were measured by means of a HITACHI 7150 Automatic Analyzer in accordance with the following procedure.

<First Reagent>
0.1 mol/L phosphate buffer
  Example 1: pH 5.5, pH 6.0, pH 6.5, pH 7.0
  Comparative Example 1: pH 7.5, pH 8.0
<Second Reagent>
5 U/mL fructosyl peptide oxidase (FPOX-CE, product of Kikkoman Corporation)
20 U/mL peroxidase (III) (product of Toyobo, Ltd.) 1 mmol/L N-ethyl-N-(2-hydroxy-3-sulfopropyl)-m-toluidine (TOOS)
1 mmol/L 4-aminoantipyrine
0.1 mol/L phosphate buffer
  Example 1: pH 5.5, pH 6.0, pH 6.5, pH 7.0
  Comparative Example 1: pH 7.5, pH 8.0
The first reagent and the second reagent employed same pH for the assay.

Each 240 μL of the first reagent was added to each 20 μL of the samples, and the resultant mixture was incubated at 37° C. for 5 minutes. Subsequently, absorbance of the mixture was measured (absorbance I). Thereafter, the second reagent (80 μL) was further added thereto, and the resultant mixture was incubated at 37° C. for 5 minutes. Subsequently, absorbance of the mixture was measured (absorbance II). Absorbance was measured at the dominant wavelength of 546 nm and non-dominant wavelength of 800 nm. The above procedure was repeated using physiological saline instead of the samples, and the resultant mixture was employed as a control (reagent containing no fV, fVH, or fK (hereinafter referred to as reagent blank)). For each sample, the difference between absorbance I and absorbance II (measurement value) was calculated by the following equation A.

$$\text{Difference in absorbance (measurement value)} = \text{Absorbance } II - (\text{Absorbance } I \times (20+240)/(20+240+80)) \quad \text{Equation A}$$

From the obtained measurement values, fK/fV values (ratio of the measurement values of ε-fructosyl lysine samples to the measurement values of fructosyl valine samples) and fK/fVH values (ratio of the measurement values of ε-fructosyl lysine samples to the measurement values of fructosyl valylhistidine samples) were calculated. The fK/fV and fK/fVH values measured at various pH conditions relative to those measured at a pH of 8.0 (100%) were compared. The results are shown in Table 1.

TABLE 1

| | Ex. 1 | | | | Comp. Ex. 1 | |
| | pH of reaction mixture | | | | | |
| | 5.5 | 6.0 | 6.5 | 7.0 | 7.5 | 8.0 |
|---|---|---|---|---|---|---|
| Ratio of measurement values: fK/fV (%) | 0.8 | 2.1 | 5.7 | 12.8 | 23.8 | 32.3 |
| Percentages with respect to fK/fV (pH 8.0) (%) | 2.5 | 6.5 | 17.6 | 39.6 | 73.7 | 100.0 |
| Ratio of measurement values: fK/fVH (%) | 1.0 | 2.5 | 6.8 | 14.9 | 27.5 | 42.2 |
| Percentages with respect to fK/fVH (pH 8.0) (%) | 2.4 | 5.9 | 16.1 | 35.3 | 65.2 | 100.0 |

As is clear from Table 1, both fK/fV values and fK/fVH values in Example 1 were found to be considerably lower than corresponding values in Comparative Example 1, which revealed that the present method provided enhanced specificity to fV and fVH and reduced reactivity to fructosyl lysines.

Example 2

Measurement of Fructosyl Amino Acid (1) Preparation of Samples

Similar to Example 1, fructosyl valylhistidine (fVH) (product of BioQuest) and ε-fructosyl lysine (fK) (product of Kikkoman Corporation) were individually dissolved in 0.02 mol/L phosphate buffer (pH 7.0) to prepare samples (0.3 mmol/L each).

(2) Measurement of Samples

The prepared samples were measured by means of a HITACHI 7150 Automatic Analyzer in accordance with the following procedure.

<First Reagent>

The first reagent in Example 1 was employed.

<Second Reagent>

The second reagent employed in Example 2 had the same composition as employed in Example 1, except that 5 U/mL fructosyl peptide oxidase (FPOX-CE) was changed to 5 U/mL fructosyl peptide oxidase (FPOX-EE).

The first reagent and the second reagent employed same pH for the assay.

The procedure of Example 1 was repeated. The results are shown in Table 2.

TABLE 2

| | Ex. 2 | | | | | | Comp. Ex. 2 |
|---|---|---|---|---|---|---|---|
| | pH of reaction mixture | | | | | | |
| | 5.5 | 6.0 | 6.5 | 7.0 | 7.5 | 8.0 | |
| fK/fVH(%) | 0.0 | 0.5 | 3.2 | 2.3 | 10.3 | 19.5 | |
| Percentages with respect to fK/fVH (pH 8.0) (%) | 0.0 | 2.6 | 16.4 | 11.8 | 52.8 | 100.0 | |

As is clear from Table 2, when fructosyl peptide oxidase (FPOX-EE) was employed instead of fructosyl peptide oxidase (FPOX-CE) employed in Example 1, fK/fVH values were found to be considerably lower than corresponding values in Comparative Example 3, revealing that the present method provides enhanced specificity to fructosyl valylhistidine and that reduced reactivity to fructosyl lysines.

Example 3

Measurement of Fructosyl Amino Acid and fructosyl Peptide (1) Preparation of Samples Fructosyl valine, fructosyl valylhistidine (these two are products of BioQuest), and ε-fructosyl lysine (product of Kikkoman Corporation) were individually dissolved in 0.02 mol/L phosphate buffer (pH 7.0) to prepare solutions (0.6 mmol/L each). To an aliquot of each of the 0.6 mmol/L fructosyl valine solutions and to an aliquot of each of the 0.6 mmol/L fructosyl valylhistidine solutions, an equiamount of 0.02 mol/L phosphate buffer (pH 7.0) was added, to thereby prepare 0.3 mmol/L fructosyl valine samples and 0.3 mmol/L fructosyl valylhistidine samples. Separately, to an aliquot of each of the 0.6 mmol/L fructosyl valine solutions and to an aliquot of 0.6 mmol/L fructosyl valylhistidine solutions, an equiamount of 0.6 mmol/L ε-fructosyl lysine solution having the same amount was added, to thereby prepare samples containing fructosyl valine (0.3 mmol/L) and ε-fructosyl lysine (0.3 mmol/L), and samples containing fructosyl valylhistidine (0.3 mmol/L) and ε-fructosyl lysine (0.3 mmol/L).

(2) Measurement of Samples

The prepared samples were measured by means of a HITACHI 7150 Automatic Analyzer in accordance with the following procedure.

<First Reagent>

Among the first reagents employed in Example 1 and Comparative Example 1, reagents (pH: 5.5, 6.5, and 8.0) were selected and employed.

<Second Reagent>

Among the second reagents employed in Example 1 and Comparative Example 1, reagents (pH: 5.5, 6.5, and 8.0) were selected and employed.

In each sample, the pH of the first reagent was the same as that of second reagent.

In a manner similar to that employed in Example 1, (fV+fK)/fV values (ratio of measurement values of samples containing fructosyl valine and ε-fructosyl lysine to measurement values of fructosyl valine samples) and (fVH+fK)/fVH values (ratio of measurement values of samples containing fructosyl valylhistidine and ε-fructosyl lysine to measurement values of fructosyl valylhistidine samples) were calculated and evaluated. The results are shown in Table 3.

TABLE 3

| | Ex. 3 | | Comp. Ex. 3 |
|---|---|---|---|
| | pH of reaction mixture | | |
| | 5.5 | 6.5 | 8.0 |
| (fV + fK)/fV (%) | 101.6 | 106.2 | 138.0 |
| (fVH + fK)/fVH (%) | 101.7 | 108.8 | 141.6 |

As is clear from Table 3, effect of ε-fructosyl lysine in Example 3 was found to be considerably lower than those of ε-fructosyl lysine in Comparative Example 3.

Example 4

Measurement of Hemoglobin A1c (HbA1c) %

(1) Preparation of Samples

Whole blood samples were taken through a routine method from 15 subjects using a blood-collection tube containing an anticoagulant EDTA. The thus-obtained whole blood samples were left to stand in a cold room overnight, whereby the erythrocytes were allowed to precipitate. An aliquot (10 μL) was sampled from each of the thus-precipitated erythrocytes was sampled. Subsequently, 0.1% aqueous Triton X-100 solution (300 μL) was added to and mixed with the thus-sampled erythrocytes (10 μL), to thereby prepare a hemolysis sample.

(2) Measurement of Samples

The prepared samples were measured by means of a HITACHI 7150 Automatic Analyzer in accordance with the following procedure.

<First Reagent>

1 U/mL proteinase K
2 mmol/L WST-3 (product of Dojindo Laboratories)
0.02 mol/L phosphate buffer (pH 8.0)

<Second Reagent>
4 U/mL fructosyl peptide oxidase (FPOX-CE, product of Kikkoman Corporation)
20 U/mL peroxidase (III) (product of Toyobo, Ltd.) 80 μmol/L DA-64 (product of Wako Pure Chemical Industries, Ltd.)
7,500 U/mL Toyozyme NEP (product of Toyobo, Ltd.)*
37.5 mmol/L NaCl
0.2 mol/L phosphate buffer (Example 4: pH 6.0, Comparative Example 4: pH 8.0)
*Before use, Toyozyme NEP (100,000 U/mL) was dialyzed against 20 mmol/L phosphate buffer (Example 4: pH 6.0, Comparative Example 4: pH 8.0) containing 500 mmol/L NaCl at 4° C. for 4 hours.
**The final pH of the reaction mixture of the present invention was 6.7, and that of the reaction mixture of Comparative Example was 8.0.

Each 240 μL of the first reagent was added to each 20 μL of the samples, and the resultant mixture was incubated at 37° C. for 5 minutes. Subsequently, absorbance of the mixture was measured (absorbance III). The second reagent (80 μL) was added thereto, and the resultant mixture was incubated at 37° C. for 5 minutes. Subsequently, absorbance of the mixture was measured (absorbance IV). For each sample, the difference between absorbance III and absorbance IV (difference=absorbance V), which was attributable to an amount of fructosyl peptide, was calculated using the following formula B.

$$\text{Absorbance } V = \text{Absorbance } IV - (\text{Absorbance } III \times (20+240)/(20+240+80)) \quad \text{Equation B}$$

The above absorbance III is proportional to the total amount of hemoglobin contained in a sample. Therefore, absorbance III and absorbance V of the sample were compared with those obtained through the above procedure from a hemocyte-hemolyzed solution having a known hemoglobin A1c value (%) (hemoglobin A1c: 8.6%), to thereby calculate hemoglobin A1c value (%) of the sample. The hemoglobin A1c values obtained in Example 4 and Comparative Example 4 were compared with that obtained through use of a commercially available kit "Rapidia A1c" (product of Fujirebio Inc., based on the latex method) (referential method). The results are shown in Table 4.

TABLE 4

| | HbA1c value (%) | | |
|---|---|---|---|
| Sample No. | Ex. 4 | Comp. Ex. 4 | Ref. Ex. |
| 1 | 5.2 | 10.0 | 6.0 |
| 2 | 4.5 | −17.0 | 5.8 |
| 3 | 5.4 | −7.2 | 6.9 |
| 4 | 5.0 | −4.4 | 5.7 |
| 5 | 4.5 | −31.4 | 5.2 |
| 6 | 3.9 | −22.4 | 4.7 |
| 7 | 4.4 | −28.7 | 4.8 |
| 8 | 5.5 | −8.3 | 7.0 |
| 9 | 5.9 | 5.6 | 7.2 |
| 10 | 6.8 | 5.9 | 7.5 |
| 11 | 6.8 | −2.9 | 8.4 |
| 12 | 9.1 | 49.1 | 8.8 |
| 13 | 8.2 | 23.9 | 8.7 |
| 14 | 8.9 | 27.1 | 9.6 |
| 15 | 11.5 | 11.5 | 11.5 |
| Correlation coefficient | 0.97 | 0.74 | |

As is clear from Table 4, with the method of Comparative Example 4, unrealistic negative HbA1c values (%) resulted, whereas HbA1c values (%) obtained through the method according to the present invention exhibited good correlation with those of the referential method, as compared with Comparative Example 4. These results show that the method according to the present invention enables determination of hemoglobin A1c value (%) in a sample while preventing effect of hemoglobin-derived ε-fructosyl lysine or fructosyl lysyl peptide.

Example 5

Measurement of Hemoglobin A1c Value (%)

(1) Preparation of Samples
Hemocyte hemolysis samples were prepared from 35 human hemocyte samples in a manner similar to that employed in Example 4.
(2) Measurement of Samples
The prepared samples were measured by means of a HITACHI 7150 Automatic Analyzer in accordance with the following procedure.
<First Reagent>
1 U/mL Proteinase K
0.2% Plysurf A208B (product of DAI-ICHI KOGYO SEIYAKU Co., Ltd.)
0.02 mol/L phosphate buffer (pH 8.0)
<Second Reagents>
4 U/mL fructosyl peptide oxidase (FPOX-CE, product of Kikkoman Corporation)
20 U/mL peroxidase (III) (product of Toyobo, Ltd.)
80 μmol/L TPM-PS (product of Dojindo Laboratories)
7,500 U/mL Toyozyme NEP (product of Toyobo, Ltd.)* 37.5 mmol/L NaCl
0.2 mol/L phosphate buffer (pH: 5.5, 6.0, 7.0, and 8.0)
*Before use, each Toyozyme NEP (100,000 U/mL) was dialyzed against 20 mmol/L phosphate buffer (pH: 5.5, 6.0, 7.0, and 8.0 respectively) containing 500 mmol/L NaCl at 4° C. for 4 hours.

Each 240 μL of the first reagent was added to each 20 μL of the samples, and absorbance of the resultant mixtures were measured at 600 nm (absorbance VI) by the comparison with the reagent blank, which is treated in the same manner except that physiological saline was employed instead of sample. Subsequently, these samples and the control were incubated at 37° C. for 5 minutes, and the second reagent (80 μL) was added thereto, followed by incubating at 37° C. for 5 minutes. Absorbance of each of the resultant mixtures was measured at 600 nm employing the reagent blank as a control (absorbance VII). These four reaction mixtures were found to have a final pH of 6.4, 6.7, 7.2, and 8.0, respectively. Hemoglobin A1c values (%) were calculated in a manner similar to that employed in Example 4. Separately, as a referential example, hemoglobin A1c values (%) of each of the reaction mixtures were measured by use of commercially available kit "RAPIDIA A1c" (product of FUJIREBIO inc.) in accordance with the manufacturer's instructions. FIG. 1 shows correlation between the hemoglobin A1c values (%) obtained from Example 5 and those obtained from the referential method, and correlation between the hemoglobin A1c values (%) obtained from Comparative Example 5 and those obtained from the referential method. Table 5 shows correlation coefficients between the hemoglobin A1c values (%) obtained from the present method and those obtained from the referential method, and correlation coefficients between the hemoglobin A1c values (%) obtained from Comparative Example 5 and those obtained from the referential method, as well as mean values of percentages (% bias) of the difference between a measurement of Example 5 or Comparative Example 5 and a corresponding measurement of the referential method, with respect to the measurement of the referential method.

TABLE 5

|  | Ex. 5 | | Comp. Ex. 5 | |
| --- | --- | --- | --- | --- |
|  | Final pH | | | |
|  | 6.4 | 6.7 | 7.2 | 8.0 |
| Correlation coefficient | 0.97 | 0.96 | 0.93 | 0.93 |
| mean % bias | −6.4 | −8.6 | −23.4 | −17.9 |

The present measurement method proved to be in good agreement with the referential method. When the present method is employed, hemoglobin A1c (%) in a sample can be measured without being affected by fructosyl lysylpeptide or ε-fructosyl lysines derived from hemoglobin.

Example 6

Identification of Storage Stability of Enzyme for Measurement of Fructosyl Peptide or Fructosyl Amino Acid (1) Preparation of Enzyme Solution
Enzyme solutions were prepared by the following arrangements.
50 mmol/L buffer (pH 6.0)*
*employed buffer agents: three buffers of potassium phosphate, sodium citrate, and N-(2-acetamide)iminodiacetic acid (ADA)
5 U/mL peroxidase (III) (product of Toyobo, Ltd.)
1 U/mL fructosyl peptide oxidase (FPOX-CE, product of Kikkoman Corporation)
(2) Storing of Enzyme Solution
The above-prepared three types of enzyme solutions were left to stand at 4° C. or 37° C. overnight.
(3) Enzyme Activity Measurement of Enzyme Solutions
Enzyme activity of the enzyme solutions was measured by means of a HITACHI 7170 Automatic Analyzer in accordance with the following procedure.
<Diluted Enzyme Solution>
Three types of enzyme solutions which had been diluted 2 fold with 100 mmol/L phosphate buffer (pH 7.5) were used in the measurement.
<First Reagent for Enzyme Activity Measurement>
0.5 mmol/L N-ethyl-N-(2-hydroxy-3-sulfopropyl)-m-toluidine (TOOS)
0.5 mmol/L 4-aminoantipyrine
1 U/mL peroxidase (III) (product of Toyobo, Ltd.)
100 mmol/L phosphate buffer (pH 7.5)
<Second Reagent for Enzyme Activity Measurement>
150 mmol/L aqueous fructosyl glycine solution
Each 182 μL of the first reagent for enzyme activity measurement was added to each 6.5 μL of the diluted enzyme solutions, and the resultant mixture was incubated at 37° C. for 5 minutes. Subsequently, each 26 μL of the second reagents for enzyme activity measurement was added to the reaction mixture. Two to three minutes after addition of the second reagent, change in absorbance at 546 nm was measured. The ratio, as expressed by %, of change in absorbance obtained from the enzyme solution which had been incubated at 37° C. to change in absorbance obtained from the enzyme solution which had been incubated at 4° C. (100%) was used for evaluation of stability.

The relative activity values obtained through use of potassium phosphate buffer, sodium citrate buffer, and ADA buffer were found to be 95%, 98%, and 89%, respectively, revealing that these buffers are excellent in storage stability of the assay enzyme of fructosyl peptide or fructosyl amino acid.

The invention claimed is:

1. A method for reducing the effect of a fructosyl lysine compound in an assay of a glycated protein-containing sample, the method comprising
treating the sample with a protease to release free fructosyl valine or fructosyl valylhistidine,
reacting a fructosyl peptide oxidase with the released fructosyl valine or fructosyl valylhistidine in the sample at a pH of 4.0 to 7.0 to produce hydrogen peroxide thereby reducing the effect of fructosyl lysine compound in the assay,
measuring the hydrogen peroxide at a pH of 4.0 to 7.0; and
correlating the measuring of the hydrogen peroxide to the presence or level of glycated protein in the sample.

2. A method according to claim 1, wherein the glycated protein is a glycated hemoglobin.

3. The method of claim 1 or 2, wherein the protease is obtained from:
(a) a microorganism belonging to a genus selected from the group consisting of *Bacillus*, *Aspergillus*, and *Streptomyces*, or
(b) a gene of the microorganism of (a) through a gene recombination technology.

4. The method of claim 1, wherein the enzyme for assaying fructosyl valine or fructosyl valylhistidine is a fructosyl peptide oxidase.

5. A reagent for assaying glycated protein with reduced effect of a fructosyl lysine compound, which comprises:
(A) a protease;
(B) an oxidase which specifically acts on fructosyl valine or fructosyl valylhistidine at a pH of 4.0 to 7.0 to thereby produce hydrogen peroxide; and
(C) a reagent for measuring hydrogen peroxide.

6. A method for reducing the effect of a fructosyl lysine compound in an assay of fructosyl valine or fructosyl valylhistidine in a sample, the method comprising:
reacting at least one of the following (A) to (C) with free fructosyl valine or fructosyl valylhistidine at a pH of 4.0 to 7.0 after the sample has been reacted with a protease to release free fructosyl valine or fructosyl valylhistidine; and recovering a product resulting from the action of (A) to (C) in the presence or absence of fructosyl valine or fructosyl valylhistidine in the sample
(A) a fructosyl peptide oxidase,
(B) a reagent for measuring hydrogen peroxide, and
(C) a glucosone-oxidizing and decomposing enzyme.

7. A method for reducing the effect of a fructosyl lysine compound in an assay of glycated protein contained in a sample, comprising: treating the sample with a protease to thereby release fructosyl valine or fructosyl valylhistidine;
reacting a fructosyl peptide oxidase, a reagent for measuring hydrogen peroxide, or a glucosone-oxidizing and decomposing enzyme with released fructosyl valine or fructosyl valylhistidine at a pH of 4.0 to 7.0 in the presence or absence of a glycated protein in the sample.

8. The method of claim 7, wherein the glycated protein is a glycated hemoglobin.

9. The method of claim 7 or 8, wherein the protease is obtained from (A) a microorganism belonging to a genus selected from the group consisting of *Bacillus, Aspergillus*, and *Streptomyces*, or (B) is obtained from a gene of the microorganism of (A) through a gene recombination technology.

10. The method of claim 6 or 7, wherein the enzyme for assaying fructosyl valine or fructosyl valylhistidine is a fructosyl peptide oxidase.

* * * * *